(12) United States Patent
Stafford-Nelson

(10) Patent No.: US 9,757,762 B2
(45) Date of Patent: Sep. 12, 2017

(54) APPARATUS AND METHOD FOR APPLYING A PRODUCT TO SKIN

(75) Inventor: Christopher Stafford-Nelson, Coventry (GB)

(73) Assignee: CRYSTALS LTD, Haddington, Scotland (GB)

( * ) Notice: Subject to any disclaimer, the term of this patent is extended or adjusted under 35 U.S.C. 154(b) by 296 days.

(21) Appl. No.: 13/810,121

(22) PCT Filed: Apr. 8, 2011

(86) PCT No.: PCT/GB2011/050694
§ 371 (c)(1),
(2), (4) Date: Mar. 20, 2013

(87) PCT Pub. No.: WO2012/007730
PCT Pub. Date: Jan. 19, 2012

(65) Prior Publication Data
US 2013/0180449 A1    Jul. 18, 2013

(30) Foreign Application Priority Data

Jul. 15, 2010 (GB) .................................. 1011917.0
Oct. 14, 2010 (GB) .................................. 1017410.0

(51) Int. Cl.
*B05C 15/00* (2006.01)
*A61M 35/00* (2006.01)
(Continued)

(52) U.S. Cl.
CPC ............. *B05C 15/00* (2013.01); *A61M 35/00* (2013.01); *B05B 12/122* (2013.01);
(Continued)

(58) Field of Classification Search
CPC ... B05C 15/00; B05B 12/122; B05B 13/0405; B05B 13/0421; A61M 35/00
See application file for complete search history.

(56) References Cited

U.S. PATENT DOCUMENTS

2004/0073186 A1* 4/2004 Cameron ...................... 604/389
2005/0022807 A1* 2/2005 Laughlin .................. 128/200.23
(Continued)

FOREIGN PATENT DOCUMENTS

WO    WO 2007/122659    11/2007

OTHER PUBLICATIONS

International Search Report for International Application No. PCT/GB2011/050694 dated Jul. 22, 2011.

*Primary Examiner* — Dah-Wei D Yuan
*Assistant Examiner* — Stephen Kitt
(74) *Attorney, Agent, or Firm* — Womble Carlyle Sandridge & Rice, LLP

(57) ABSTRACT

An apparatus (100) for applying product to the skin of a person in a booth (10), comprising: an applicator (57) configured to apply the product to the person; a first guide (40) configured to guide movement of an applicator in a first dimension, in order to enable the applicator to apply the product to the person at a plurality of different heights; and a second guide (20) configured to guide movement of the applicator in a second dimension, in order to enable the applicator to apply the product across the width of the person. The apparatus may comprise control circuitry for controlling the applicator in dependence upon the weight of the person.

20 Claims, 12 Drawing Sheets

(51) Int. Cl.
 *B05B 12/12* (2006.01)
 *B05B 13/04* (2006.01)
 *G07F 17/18* (2006.01)
(52) U.S. Cl.
 CPC ...... *B05B 13/0405* (2013.01); *B05B 13/0421* (2013.01); *G07F 17/18* (2013.01)

(56) References Cited

U.S. PATENT DOCUMENTS

| | | |
|---|---|---|
| 2006/0032439 A1 | 2/2006 | Burato et al. |
| 2007/0197982 A1* | 8/2007 | Thomason et al. ........... 604/289 |
| 2010/0001097 A1 | 1/2010 | Spivak |
| 2010/0162951 A1* | 7/2010 | Pinotti ......................... 118/642 |

\* cited by examiner

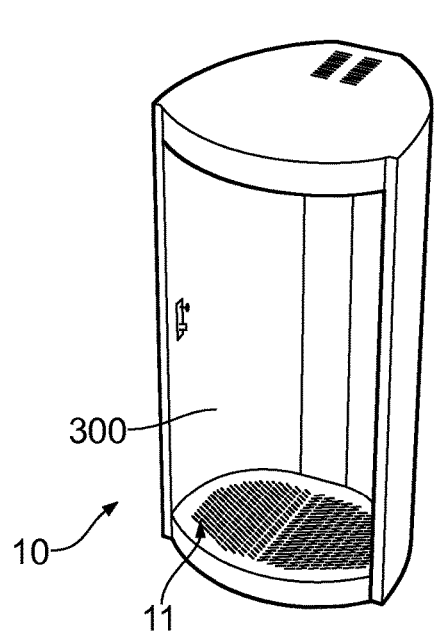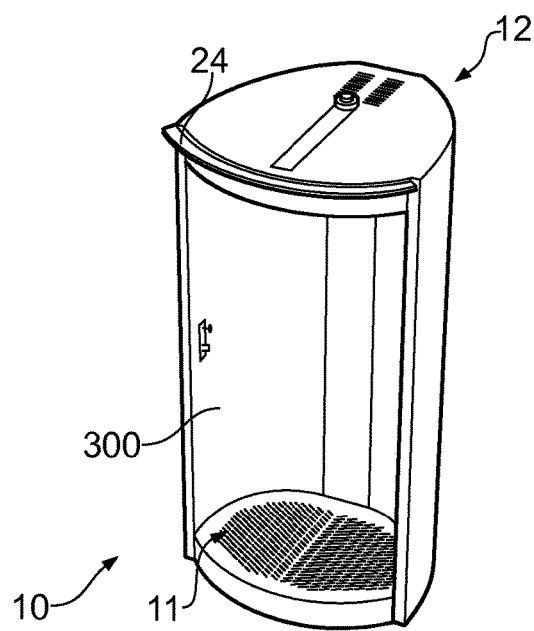
FIG. 3A    FIG. 3B
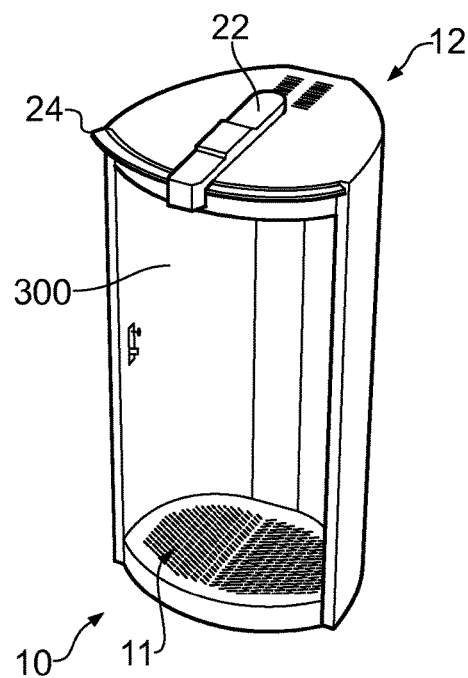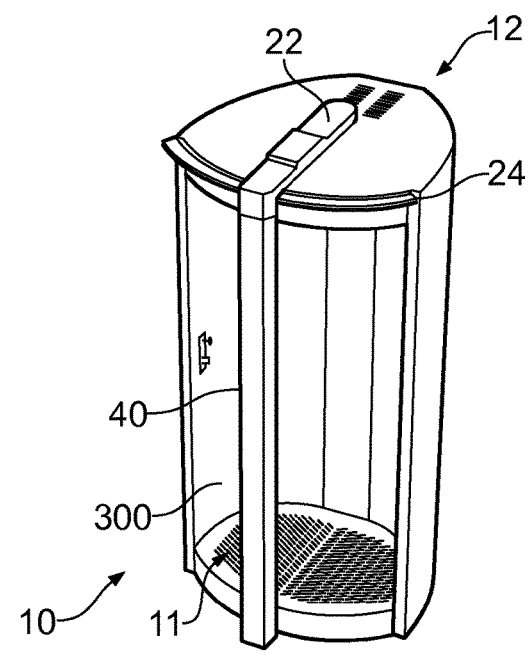
FIG. 3C    FIG. 3D

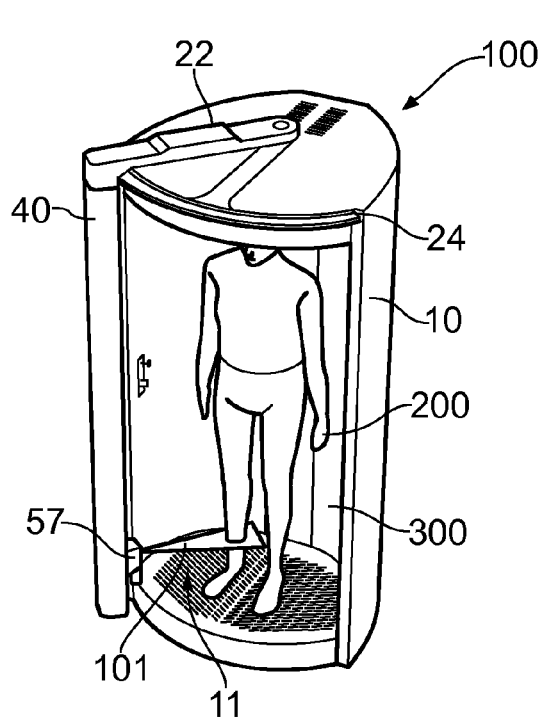
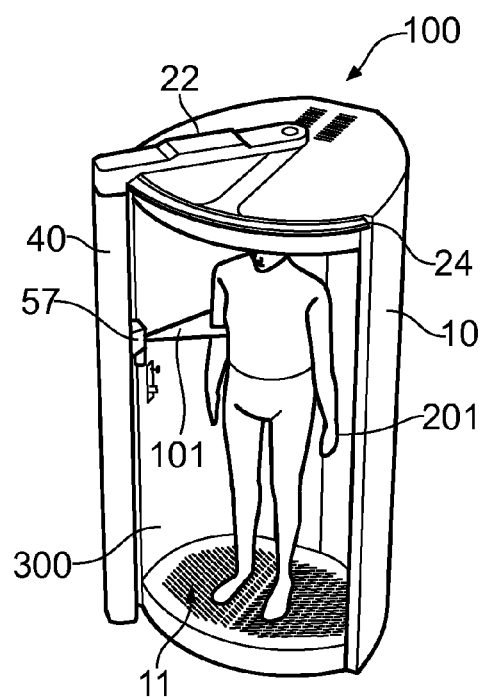
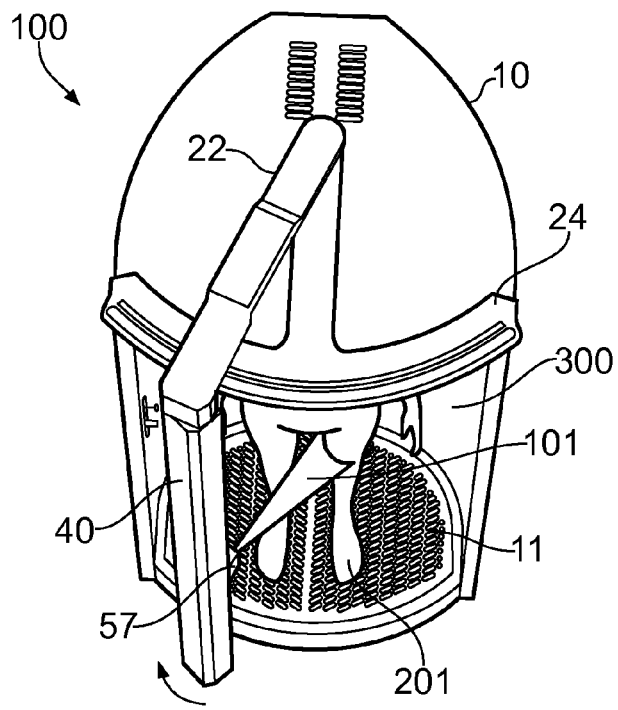
FIG. 5A
FIG. 5B
FIG. 5C

APPARATUS AND METHOD FOR APPLYING A PRODUCT TO SKIN

TECHNOLOGICAL FIELD

Embodiments of the present invention relate to the application of a product to the skin of a person. In particular, they relate to applying skin product, such as sunless tanning lotion, to the skin of a person in a booth.

BACKGROUND

In recent years, tanning booths have become popular. A person may, for example, stand within such a tanning booth while sunless tanning lotion is applied to him/her by a human operator or by automated means.

In circumstances where the sunless tanning lotion is applied using automated means, it can be difficult to ensure that sunless tanning lotion is applied to the person in an even fashion and in a manner that is comfortable for the person.

BRIEF SUMMARY

According to some, but not necessarily all, embodiments of the invention, there is provided an apparatus for applying product to the skin of a person in a booth, comprising: an applicator configured to apply the product to the person; a first guide configured to guide movement of the applicator in a first dimension, in order to enable the applicator to apply the product to the person at a plurality of different heights; and a second guide configured to guide movement of the applicator in a second dimension, in order to enable the applicator to apply the product across the width of the person.

The second guide may be configured to guide movement of the applicator in the second dimension by guiding the first guide in the second dimension. The second guide may be configured to guide the applicator along an arcuate path.

The first guide may have a length extending in the first dimension.

The applicator may be configured to rotate about an axis of rotation aligned with the length of the first guide. The applicator may be configured to rotate by substantially 70 degrees.

The second guide may be configured to cause the first guide to rotate about an axis of rotation that is separated from, and substantially parallel with, the length of the first guide. The second guide may be configured to cause the first guide to rotate by substantially 90 degrees.

The apparatus may further comprise: a first drive configured to drive the applicator along the first guide and in the first dimension; and a second drive configured to drive the first guide in the second dimension.

The apparatus may further comprise: control circuitry configured to control the first drive and the second drive in accordance with a product application program. The product application program used by the control circuitry may depend on the weight of the person to whom the product is to be applied. The product application program used by the control circuitry may depend on the height of the person to whom the product is to be applied.

The apparatus may further comprise: a sensor configured to sense the height of the person to whom the product is to be applied. The apparatus may further comprise: a sensor configured to sense the weight of the person to whom the product is to be applied.

The apparatus may further comprise: a sensor configured to sense resistance to movement of the first guide in the second dimension, and control circuitry configured, in response to the sensor sensing resistance to movement of the first guide in the second dimension, to cause the first guide to cease.

The applicator may be a spray gun configured to spray the product onto the skin of the person. The spray gun may have a variable fan output size. The apparatus may further comprise control circuitry for controlling the fan output size in dependence upon the weight of the person to be sprayed.

According to some, but not necessarily all, embodiments of the invention, there is provided an apparatus, comprising: control circuitry; and at least one memory storing computer program instructions that, when executed by the control circuitry, cause the apparatus to perform at least the following: controlling guided movement of an applicator in a first dimension, in order to enable the applicator to apply product to the skin of a person at a plurality of different heights; and controlling guided movement of the applicator in a second dimension, in order to enable the applicator to apply the product across the width of the person.

According to some, but not necessarily all, embodiments of the invention, there is provided a method, comprising: controlling guided movement of an applicator in a first dimension, in order to enable the applicator to apply product to the skin of a person at a plurality of different heights; and controlling guided movement of the applicator in a second dimension, in order to enable the applicator to apply the product across the width of the person.

According to some, but not necessarily all, embodiments of the invention, there is provided a non-transitory computer readable medium storing computer program instructions that, when executed by control circuitry, cause at least the following to be performed: controlling guided movement of an applicator in a first dimension along a first guide, in order to enable the applicator to apply product to the skin of a person at a plurality of different heights; and controlling guided movement of the applicator in a second dimension, in order to enable the applicator to apply the product across the width of the person.

According to some, but not necessarily all, embodiments of the invention, there is provided an apparatus for applying product to the skin of a person in a booth, comprising: an applicator configured to apply the product to the person; and control circuitry for controlling the applicator in dependence upon the weight of the person.

According to some, but not necessarily all, embodiments of the invention, there is provided an apparatus, comprising: control circuitry; and at least one memory storing computer program instructions that, when executed by the control circuitry, cause the apparatus to perform at least the following: determining the weight of a person; and controlling an applicator, for applying the product to the person, in dependence upon the weight of the person.

According to some, but not necessarily all, embodiments of the invention, there is provided a method for applying product to the skin of a person in a booth, comprising: determining the weight of a person; and controlling an applicator, for applying the product to the person, in dependence upon the weight of the person.

According to some, but not necessarily all, embodiments of the invention, there is provided a non-transitory computer readable medium storing computer program instructions that, when executed by control circuitry, cause at least the following to be performed: determining the weight of a person; and controlling an applicator, for applying the product to the person, in dependence upon the weight of the person.

BRIEF DESCRIPTION

For a better understanding of various examples of embodiments of the present invention reference will now be made by way of example only to the accompanying drawings in which:

FIGS. 3A to 3D illustrate the addition of first and second guides to a booth;

FIGS. 5A to 5C illustrate product being applied to the skin of a person in a booth;

DETAILED DESCRIPTION

Figure 1:
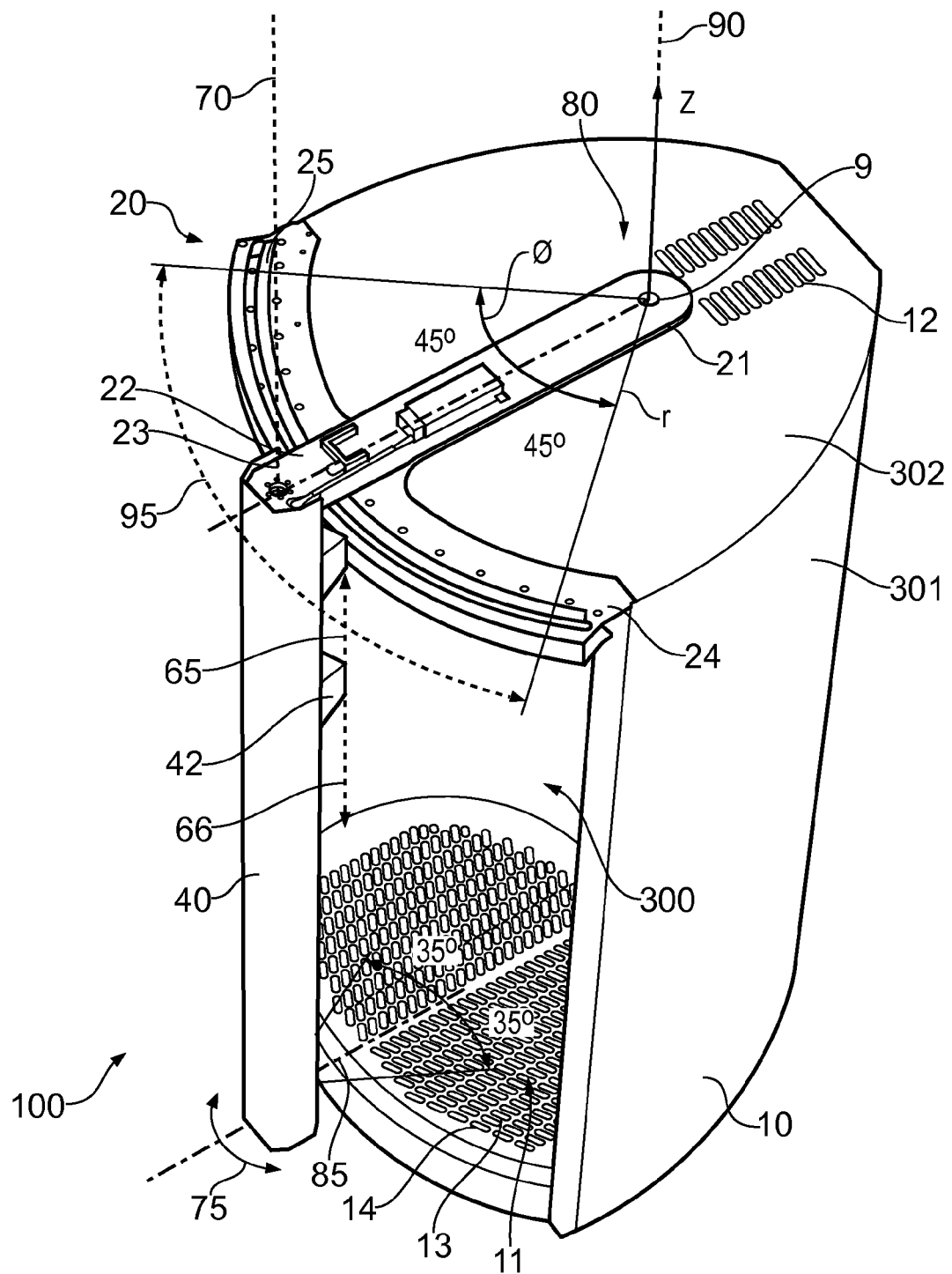
FIG. 1 illustrates an apparatus for applying product to the skin of a person.

Embodiments of the invention provide an efficient method of evenly applying skin product, such as tanning lotion, to the skin of a person.

The Figures illustrate an apparatus 100 for applying product to the skin of a person 200/201 in a booth 10, comprising: an applicator 57 configured to apply the product to the person 200/201; a first guide 40 configured to guide movement of the applicator 57 in a first dimension z, in order to enable the applicator 57 to apply the product to the person 200/201 at a plurality of different heights; and a second guide 20 configured to guide movement of the applicator 57 in a second dimension ϕ, in order to enable the applicator 57 to apply the product across the width of the person 200/201/202.

FIG. 1 illustrates an apparatus 100 for applying product to the skin of a person in a booth 10. The apparatus 100 may or may not comprise the booth 10. For example, in some embodiments of the invention, the apparatus 100 does not comprise the booth 10 and is supplied as a kit of parts for attachment to an existing booth. The booth 10 illustrated in FIG. 1 comprises a base 13 having a foot grate 14, a roof 12, and an entrance/front opening 11.

The booth 10 is an enclosure that defines an inner volume 300. In this example, one or more walls 301, 302 of the booth 10 define the booth volume 300.

The front opening 11 of the booth 10 is shaped so as to enable a person to enter the booth 10 via the front opening 11 (e.g. by walking) and position himself (entirely) within the booth volume 300. When product is to be applied to the skin of a person, the person enters the booth 10 via the front opening 11 and stands in the booth volume 300 and on the foot grate 14. In this particular example, the booth 10 does not comprise a door for covering the front opening 11.

The apparatus 100 comprises a first guide 40 and a second guide 20. The second guide 20 comprises an arm 22 and a track member 24. A first end 21 of the arm 22 is rotatably attached to the roof 12 of the booth 10 at the point designated by the reference numeral 9. A second end 23 of the arm 22 is fixedly connected to the first guide 40. The first guide 40 is elongate in shape and has the form of a column. The first guide 40 has a length that extends, perpendicular to the arm 22, down the front opening 11 of the booth 10.

The track member 24 is fixedly connected to the roof 12 of the booth 10, above the front opening 11. The track member 24 comprises a curved track 25 which may, for example, be a gear rack. The arm 22 is configured to move along the track 25 of the track member 24. The arm 22 may, for example, comprise a pinion that enables the arm 22 to move along the track 25.

FIG. 1 illustrates a cylindrical co-ordinate system 80 with an azimuthal dimension ϕ, a radial dimension r and a longitudinal dimension z. Each of the dimensions ϕ, r and z are orthogonal to one another. The illustrated co-ordinate system 80 is centred on the point 9 at which the arm 22 is connected to the booth 10.

The arm 22 is configured to rotate about its connection point 9 and the axis of rotation designated with the reference numeral 90. The arm 22 rotates in the azimuthal dimension ϕ and extends in the radial dimension r outwardly from the connection point 9. FIG. 1 illustrates an example in which the arm 22 is configured to rotate about the axis 90 by 90 degrees. In FIG. 1, the arm 22 is illustrated as being in a central position, relative to its range of motion.

As mentioned above, the first guide 40 is fixedly connected to the second end 23 of the arm 22. The length of the first guide 40 extends in the longitudinal dimension z. Movement of the arm 22 (of the second guide 20) in the azimuthal dimension ϕ causes the first guide 40 to move in the azimuthal dimension ϕ. The second guide 20 is therefore configured to guide the first guide 40, along an arcuate path, in the azimuthal dimension ϕ. As the first guide 40 moves, it remains perpendicular to the arm 22. There is no movement of the first guide 40 in the radial and longitudinal dimensions r, z. The arrow 95 indicates the direction of movement of the arm 22 along the track 25 and the direction of movement of the first guide 40.

The first guide 40 is positioned outside the booth volume 300 and is configured to guide an applicator 57 in the longitudinal dimension z. At least part of the applicator 57 may be contained within the first guide 40. The applicator 57 is configured to apply product to the skin of a person positioned in the booth 10. In this example, the applicator 57 applies product through the front opening 11 and onto the skin of a person positioned in the booth 10 (e.g. by spraying product through the front opening 11).

The product that is applied to the skin of the person may be a beauty product for example, such as sunless tanning lotion. The applicator 57 may, for example, be a spray applicator (such as a spray gun) that is configured to spray the product onto the skin of a person in the booth 10.

In the example illustrated in FIG. 1, the applicator 57 is positioned in a carriage 42 that is arranged to slide along the first guide 40 in the longitudinal dimension z. The arrows 65 and 66 indicate the directions of movement of the carriage 42 and the applicator 57 along the first guide 40.

The first guide 40 enables the applicator 57 to move to various different positions in the longitudinal dimension z, and therefore enables the applicator 57 to apply product to a person positioned in the booth 10 at a plurality of different heights.

The second guide 20 guides the movement of the applicator 57 in the azimuthal dimension ϕ by guiding the first guide 40 across the front opening 11 of the booth 10. The first guide 40 may, for example, move to various different azimuthal positions across the front opening 11. This enables the applicator 57, situated in the first guide 40, to move across the front opening 11 and apply product across the width of a person positioned in the booth 10.

The applicator 57 is also configured to rotate, in the azimuthal dimension φ, about an axis of rotation 70 that is aligned with the length of the first guide 40, and separate from the axis of rotation 90 of the arm 22. The axis of rotation 70 is aligned with the longitudinal dimension z and is substantially parallel with the axis of rotation 90 of the arm 22.

The arrow designated with the reference numeral 75 is illustrative of the movement of the applicator 57. The applicator 57 may, for example, be configured to rotate about its axis of rotation 70 by substantially 70 degrees. In the example illustrated in FIG. 1, the applicator 57 is directed towards the centre of the opening 11 in the booth 10, as illustrated by the line 85.

Figure 2A:
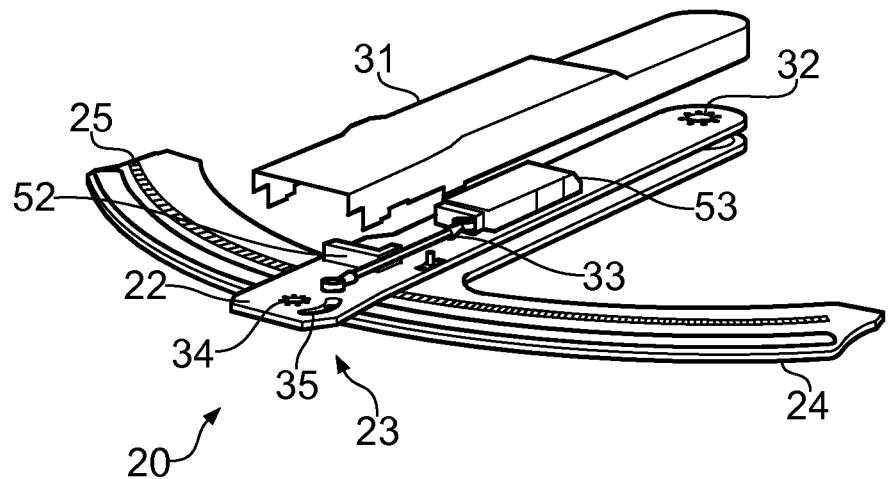
FIG. 2A illustrates a guide comprising a track member and an arm.

The second guide 20 is illustrated in more detail in FIG. 2A. It can be seen in FIG. 2A that the arm 22 comprises at least one aperture 32 for use in rotatably connecting the arm 22 to the roof 12 of the booth 10. The arm 22 also comprises at least one aperture 34 for use in connecting the arm 22 to the first guide 40.

FIG. 2A also illustrates a drive 52, situated on the arm 22, which is configured to drive the arm 22 along the track 25. In this example, the drive 52 is a stepper motor that rotates a pinion, driving the arm 22 along the track 25 in discrete steps and causing the first guide 40 to move along the azimuthal dimension φ in discrete steps.

A further drive 53 is also situated on the arm 52. The further drive 53 is configured to cause the applicator 57 to rotate about the axis 70. The operation of the drive 53 can be seen in FIGS. 2B and 2C. The drive 53 may, for example, be a linear drive that is configured to move a first link member 33, in the form of a rod, in a linear fashion. The first link member 33 is elongate in shape and extends along the arm 22 in the radial dimension r. The first link member 33 is coupled to a second member 36 which extends through an aperture 37 in the arm 22 and down the first guide 40 in the longitudinal dimension z. The second link member 36 is coupled to the applicator 57.

The aperture 37 in the arm 22 includes a curved peripheral surface 35. The curved peripheral surface 35 acts as a cam, causing the linear motion of the first link member 33 to be converted into rotational motion of the applicator 57 coupled to the second link member 36.

Figure 2B:
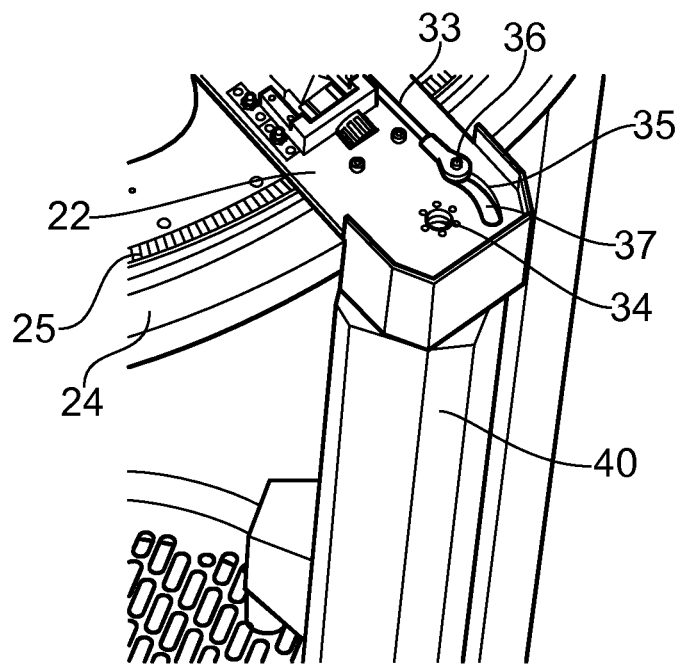
FIGS. 2B and 2C illustrate an end portion of the arm connected to a vertical guide.
Figure 2C:
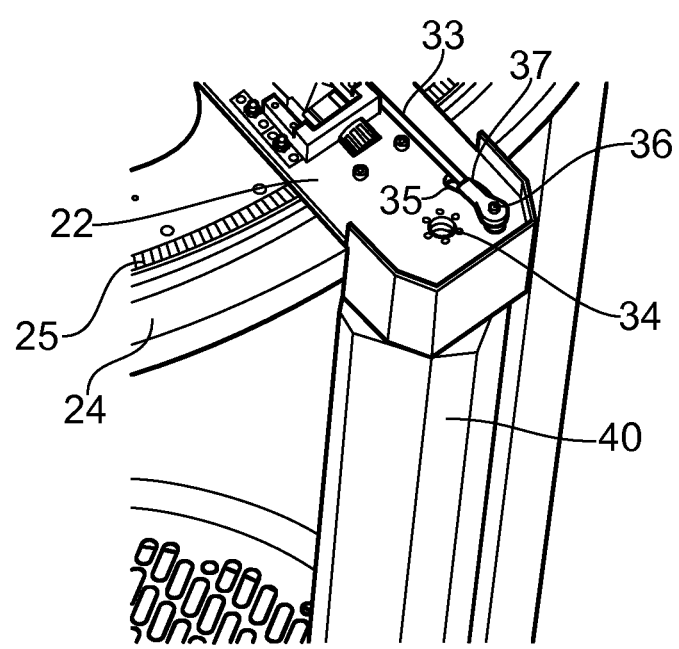

FIG. 2B illustrates the first link member 33 at one extremity of its motion and FIG. 2C illustrates the first link member 33 at the opposite extremity of its motion.

As can be seen in FIG. 2A, a cover 31 may be provided to cover the components situated on the arm 22.

FIGS. 3A to 3D illustrate the apparatus 100 being fitted in steps to an existing booth 10. FIG. 3A illustrates a booth 10. FIG. 3B illustrates the booth 10 after the track member 24 of the second guide 20 has been fitted to the roof 12 of the booth 10. FIG. 3C illustrates the booth 10 after the arm 22 of the second guide 20 has been fitted to the roof 12 of the booth 10. FIG. 3D illustrates the booth 10 after the first guide 40 has been connected to the arm 22.

Figure 4:
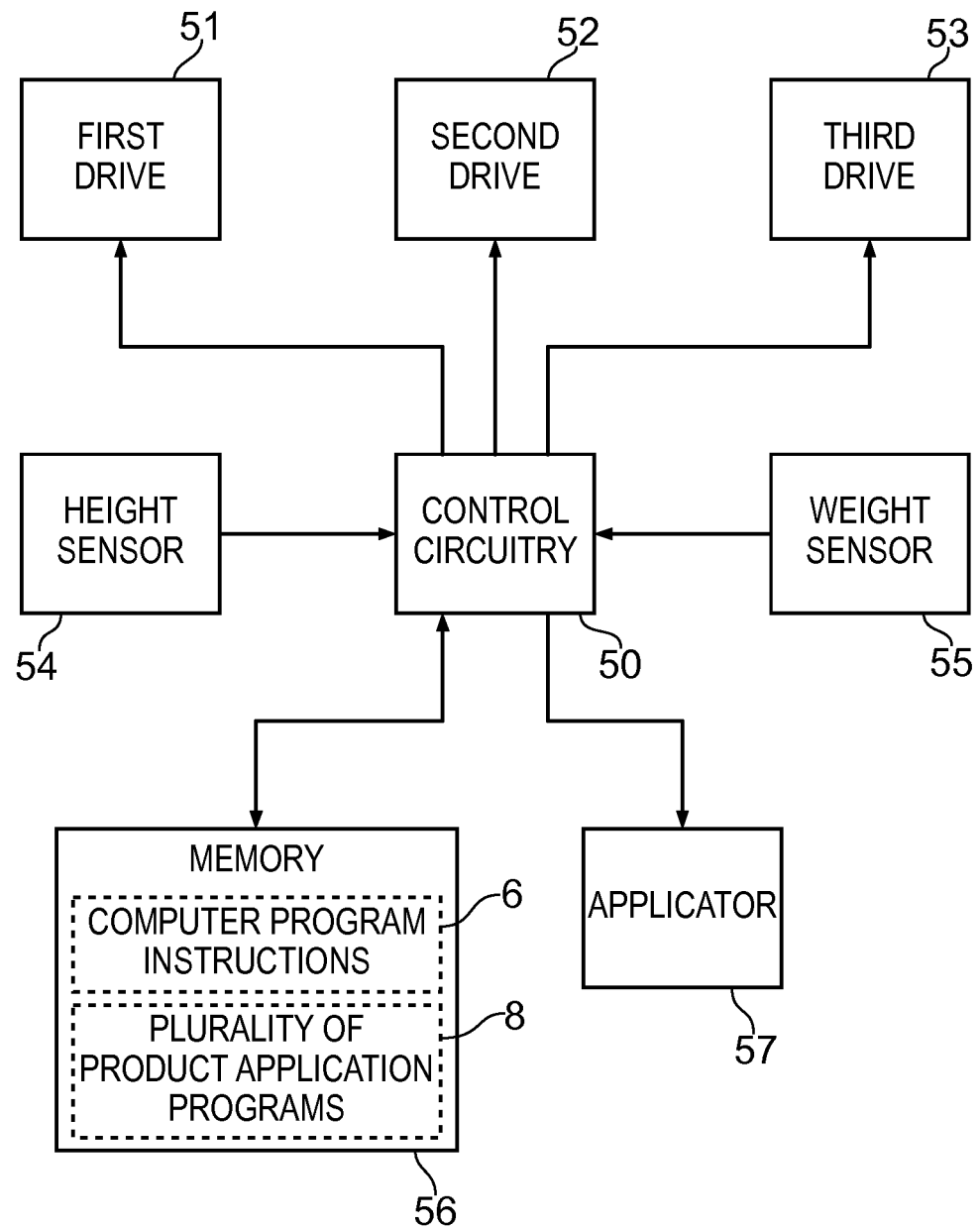
FIG. 4 illustrates a control aspect of the apparatus.

FIG. 4 illustrates components 51-57 of the apparatus 100 that receive inputs from or provide inputs to control circuitry 50 of the apparatus 100. If the apparatus 100 is a kit of parts, it may comprise some or all of the elements 50 to 57 illustrated in FIG. 4.

The elements 50-57 illustrated in FIG. 4 may be operationally coupled and any number or combination of intervening elements can exist (including no intervening elements)

The control circuitry 50 may, for example, be (or comprise) one or more processors. The control circuitry 50 is configured to provide outputs to a first drive 51, a second drive 52, a third drive 53 and the applicator 57. The control circuitry 50 is configured to receive inputs from a height sensor 54 and a weight sensor 55. The control circuitry 50 is also configured to read from and write to a memory 56.

The memory 56 stores computer program instructions 6 that control the operation of the apparatus 100 when loaded into the control circuitry 50. The computer program instructions 6 provide the logic and routines that enables the apparatus 100 to perform the method illustrated in FIG. 10. The control circuitry 50, by reading the memory 56, is able to load and execute the computer program instructions 6.

The memory 56 is a non-transitory, tangible computer readable medium. Although the memory 56 is illustrated as a single component it may be implemented as one or more separate components some or all of which may be integrated/removable and/or may provide permanent/semi-permanent/dynamic/cached storage.

The first drive 51 is configured to drive the applicator 57 along the first guide 40. Through appropriate control of the first drive 51, the control circuitry 50 is able to move and position the applicator 57 in the longitudinal dimension z.

The second drive 52 was described above and is configured to drive the arm 22 along the track 25 and to drive the first guide 40 in the azimuthal dimension φ. Through appropriate control of the first drive 51, the control circuitry 50 is able to position the first guide 40 (and therefore the applicator 57) in any one of a number of positions across the width of the front opening 11 of the booth 10.

The third drive 53 was described above and is configured to the applicator 57 to rotate about the axis 70. Through appropriate control of the third drive 53, the control circuitry 50 is able to control the direction in which the applicator 57 outputs product towards a person positioned in the booth 10.

The height sensor 54 is configured to enable the control circuitry 50 to determine the height of a person positioned in the booth 10. The height sensor 54 may, for example, be positioned in the carriage 42 that slides along the first guide 40. For instance, the height sensor 54 may be an ultrasonic sensor or a photoelectric sensor for determining the height of a person.

The weight sensor 55 is configured to enable the control circuitry 50 to determine the weight of a person positioned in the booth 10. The weight sensor 55 may, for example, be a load cell or a strain gauge for determining the weight of a person when the person steps on the foot grate 14.

As described above, the applicator 57 may, for example, be a spray gun that is configured to spray product onto the skin of a person in the booth 10. The spray gun may have a variable fan output size. In some embodiments of the invention, the applicator 57 is a "flat spray gun". The fan of product that is output by a flat spray gun is relatively 'flat' in the longitudinal dimension z (as compared with the output in the azimuthal and radial dimensions φ, r). The control circuitry 50 may be configured to control the fan output size of the applicator/spray gun 57.

It will be appreciated by those skilled in the art that the size of people using the booth 10 will vary. For example, the users will have varying heights and varying weights. The memory 56 stores a plurality of product application programs 8 for the apparatus 100. The product application programs 8 define how the control circuitry 50 should control the applicator 57, via the drives 51-53, to apply product to people of different sizes (i.e. different heights and weights). The plurality of product application programs 8 may, for example, be stored as a look-up table in the memory 56.

Each product application program may, for example, define the following:

i) The fan output size of the applicator/spray gun 57. For example, the product application programs 8 may specify that the control circuitry 50 controls the applicator/spray gun 57 to use a larger fan output size for larger bodies (i.e. larger heights and weights).

ii) The manner in which the applicator 57 is guided along the first guide 40 while the product is being applied to a person. For example, the product application programs 8 may specify that the control circuitry 50 controls the applicator 57 to apply product across a larger longitudinal distance for a larger person than for a smaller person.

If a larger fan output size has been selected, it may be appropriate to control the applicator 57 to move more slowly along the first guide 40 than if a smaller fan output size had been selected, to ensure that enough product is applied to the skin of the person.

The control circuitry 50 may be configured to determine, from the height of the person, the position of various parts of the person such as the legs, the torso and the head. It may be desirable to provide different densities of coverage of the product on different parts of the person. Consequently, the product application programs 8 may specify that the control circuitry 50 controls the applicator 57 to move at different speeds depending on the part of the body that the product is being applied to.

The apparatus 100 may be configured to provide the person with an option of selecting the density of the coverage of the product. For example, if the product is a sunless tanning lotion, the person may be able to select whether he/she wishes to have a light, medium or deep tan. The speed at which the applicator 57 moves along the first guide 40 may depend upon the selection made by the person. For example, the control circuitry 50 may control the applicator 57 to move more slowly if a dense coverage has been selected, than if a light coverage had been selected.

iii) The manner in which the applicator 57 is rotated about axis of rotation 70 when product is being applied. For example, the determined height and weight of the person will indicate a particular body size. The product application programs 8 may specify that the third drive 53 is controlled differently by the control circuitry 50, depending upon the determined size (i.e. the determined height and/or weight) of a person.

iv) The manner in which second guide 20 guides the first guide 40 in the azimuthal dimension $\phi$. For example, it may be appropriate to rotate the arm 22 across a greater angular range for a person having a larger weight than for a person having a smaller weight.

In a method according to embodiments of the invention, after a person has stepped into the booth 10, the control circuitry 50 determines, using the height sensor 54 and the weight sensor 55, the height and weight of the person to whom product is to be applied. In response, the control circuitry 50 selects an appropriate product application program 8 for a person having the determined height and weight.

The control circuitry 50 then controls the applicator 57 to begin applying product to the person using the selected product application program. In a typical product application program, the arm 22 may rotate the first guide 40 in ten incremental steps across the front opening 11 of the booth 10. For each azimuthal position of the first guide 40, the applicator 57 may apply product continuously as it moves up the first guide 40 (an "up stroke") and down the first guide 40 (a "down stroke"). An up stroke and a down stroke may be completed for each azimuthal position of the first guide 40. In some azimuthal positions, such as those close to the centre of the opening 11 of the booth 10, additional smaller up and down strokes may be performed. These additional smaller strokes may, for example, enable better coverage to be provided in traditionally difficult to reach areas, such as the inner leg.

FIG. 5A illustrates product being applied to a relatively slim person 200 positioned in the booth 10 by the applicator 57. The reference numeral 101 illustrates the fan output of product from the applicator 57. FIG. 5B illustrates product being applied to a larger person 201 by the applicator 57. FIG. 5C illustrates product being applied to the inner leg of a person by the applicator 57 when the first guide 40 is at a different azimuthal position as compared with FIGS. 5A and 5B.

An apparatus 100 for applying product to the skin of a person has been described above. The apparatus 100 is particularly advantageously because it enables a product to be applied to the skin of a person in a consistent manner. This is achieved, at least in part, by enabling the applicator 57 to be placed in a large number of positions and to be directed in a wide variety of directions. It is also achieved because the size of a person is taken into consideration when determining how to control the applicator 57 to apply product to that person.

Figure 6:
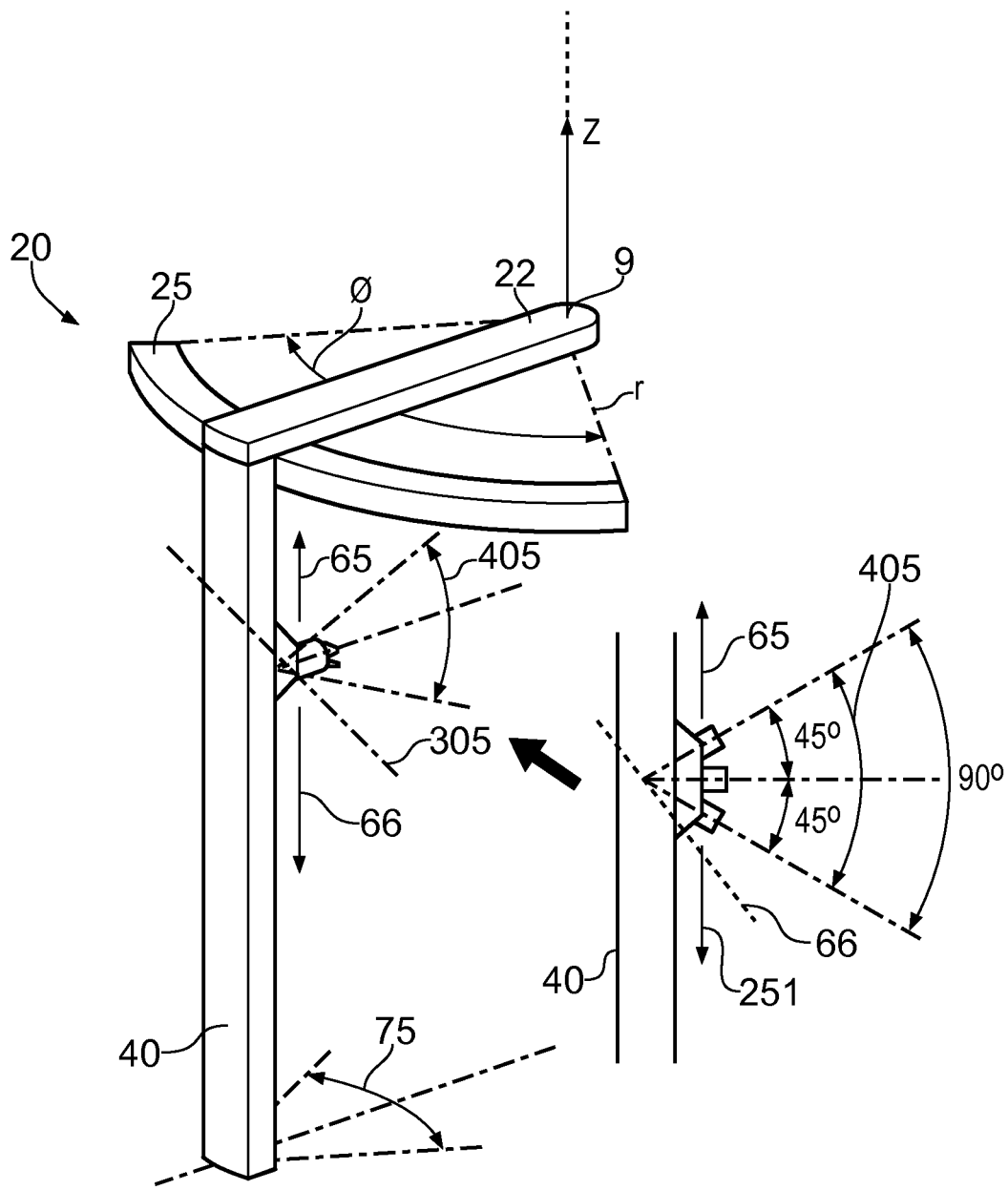
FIGS. 6 and 7 illustrate movement of an applicator of the apparatus.

FIG. 6 illustrates an embodiment of the invention in which the applicator 57 is configured to rotate about an axis 305. The movement of the applicator 57 is illustrated by the arrows designated with the reference numeral 405 in FIG. 6. The applicator 57 may be configured to rotate about the axis 305 in addition to rotating about the axis 70 illustrated in FIG. 1.

In the FIG. 6 example, the axis of rotation 305 is perpendicular to the length of the elongate first guide 40 and the axis 70. The axis 305 is also perpendicular to the length of the arm 22. The applicator 57 may, for example, be able to rotate by 90 degrees about the axis 305. The control circuitry 50 may be configured to cause the applicator 57 to rotate about the axis 305 by controlling a drive.

Rotation of the applicator 57 about the axis 305 enables the applicator 57 to direct product upwardly or downwardly, for example. The applicator 57 may, for example, be directed downwards when spraying the top of a person's shoulders. The applicator 57 may, for example, be directed upwards when spraying under a person's breasts, chin, armpits or crotch area.

The arrows 65 and 66 in FIG. 6 illustrate the directions of movement of the applicator 57 along the first guide 40.

Figure 7:
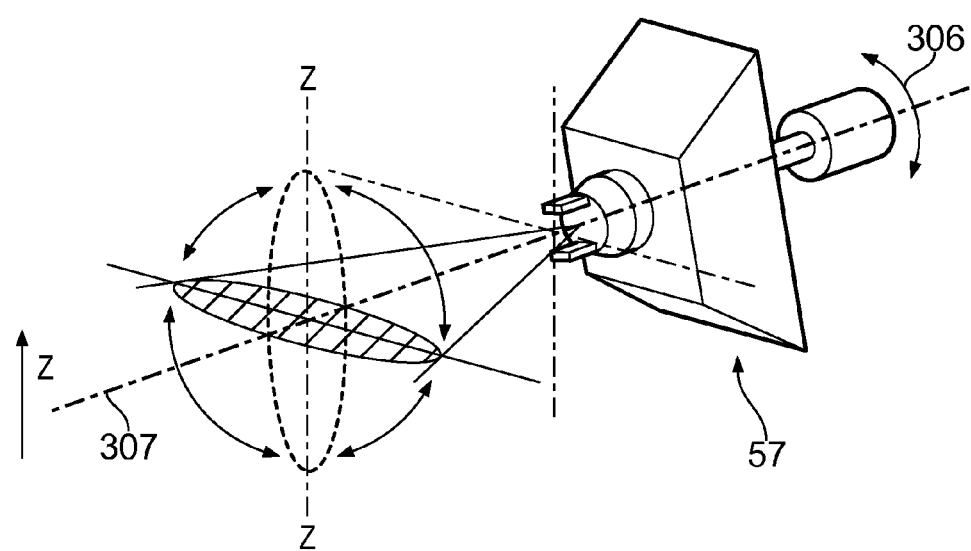

FIG. 7 illustrates an embodiment in which the applicator 57 is a flat spray gun. In the illustration, the fan of product that is produced by the applicator 57 is relatively 'flat' in the longitudinal dimension z. In this example, the applicator 57 is configured to be rotatable about the axis 307. The motion of the applicator 57 is illustrated by the arrow 306. The axis of rotation 307 is perpendicular to the longitudinal dimension z and perpendicular to the axis of rotation 305 illustrated in FIG. 6.

The control circuitry 50 may control the applicator 57 to rotate about the axis 307 via a drive.

Figure 8:
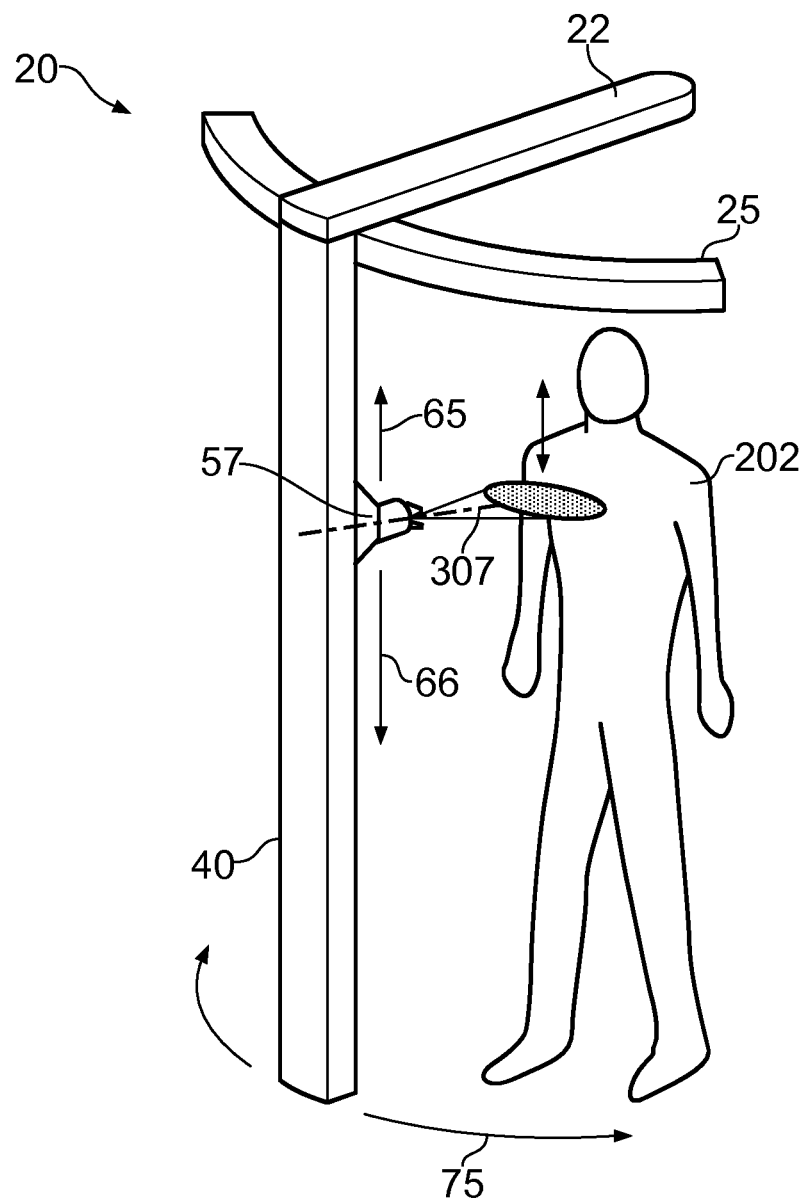
FIGS. 8 and 9 illustrate product being applied to the skin of a person.
Figure 9:
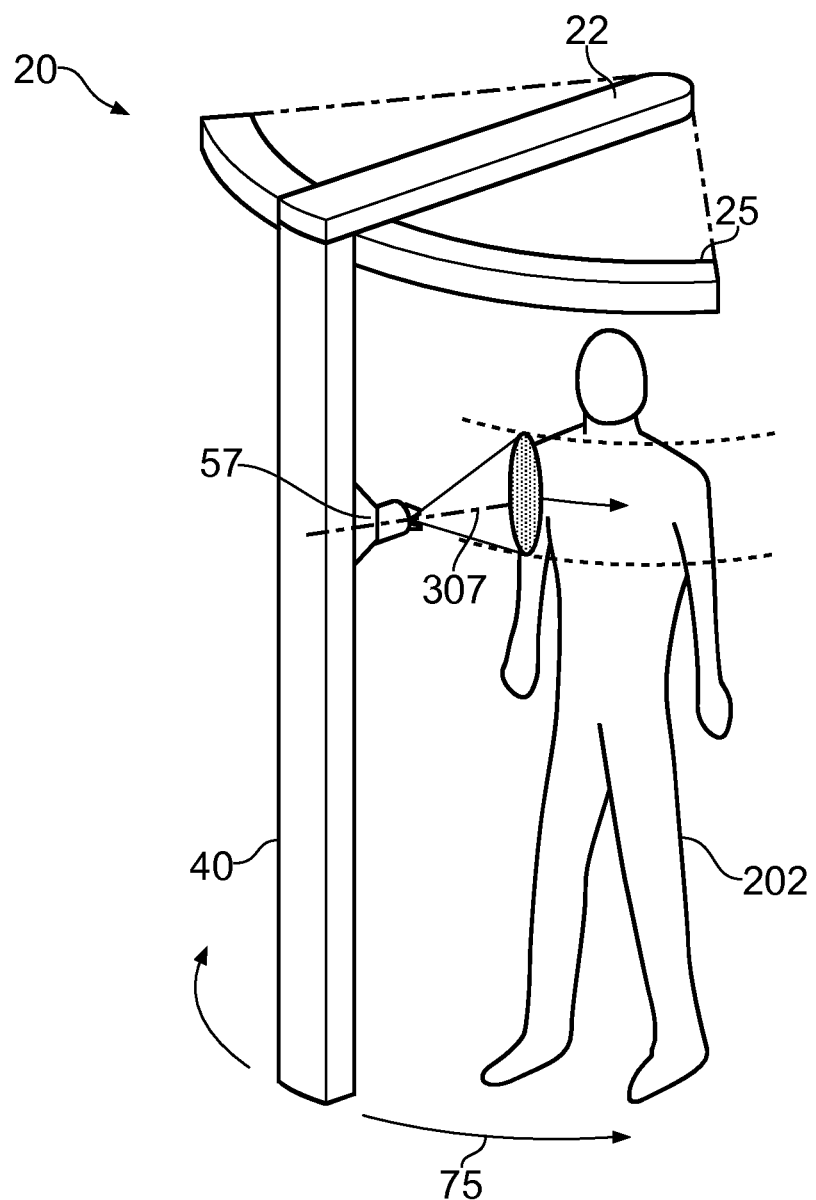

FIG. 8 illustrates product being applied to a person 202 using the applicator 57 illustrated in FIG. 7. FIG. 9 illustrates product being applied to a person 202 using the applicator 57, after the applicator 57 has been rotated by 90 degrees about the axis 307.

Figure 10:
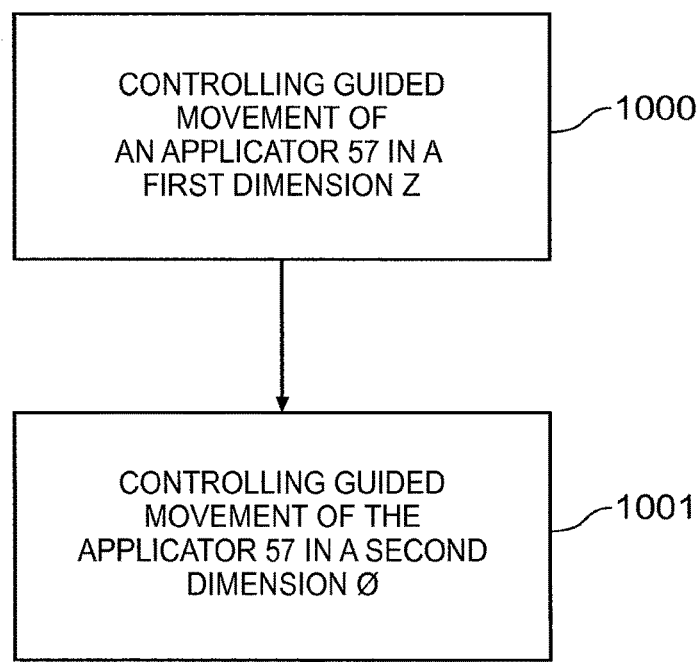
FIG. 10 illustrates a method.
Figure 11:
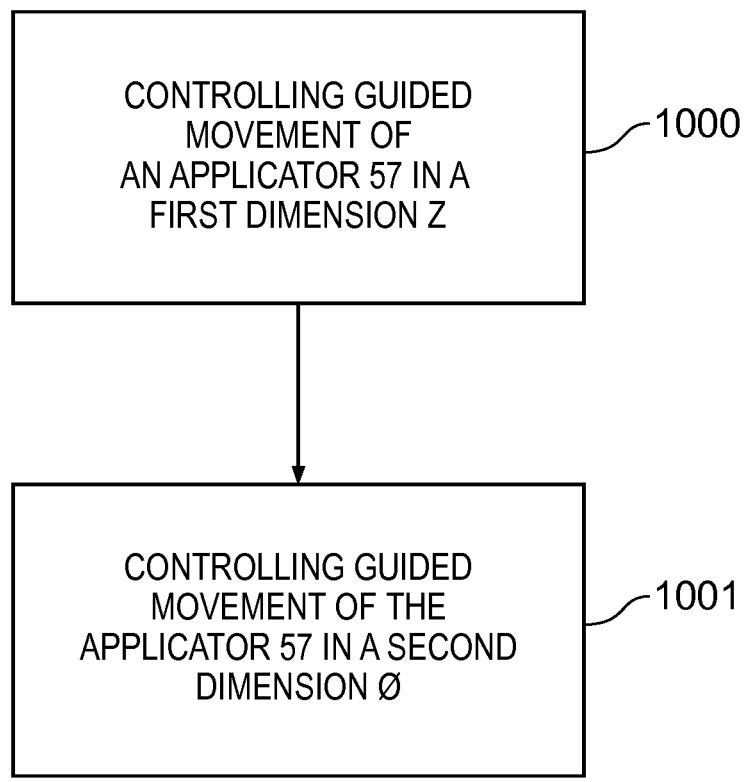

FIG. 10 illustrates a method according to embodiments of the invention. At block 1000 in FIG. 10, the control circuitry 50 controls guided movement of the applicator 57 in a first (longitudinal) dimension z (e.g. movement of the applicator 57 along the first guide 40), in order to enable the applicator 57 to apply product to the skin of a person (positioned within the booth 10) at a plurality of different heights.

At block 1001 in FIG. 10, the control circuitry 50 controls guided movement of the applicator 57 in a second (azimuthal) dimension φ (e.g. movement of the applicator 57 and the first guide 40), in order to enable the applicator 57 to apply the product across the width of the person positioned within the booth 10.

The blocks illustrated in FIG. 10 may represent steps in a method and/or sections of code in the computer program instructions 6. The illustration of a particular order to the blocks does not necessarily imply that there is a required or preferred order for the blocks and the order and arrangement of the block may be varied. Furthermore, it may be possible for some blocks to be omitted.

References to 'computer-readable storage medium', 'computer program product', 'tangibly embodied computer program' etc. or 'control circuitry', 'computer', 'processor' etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term 'circuitry' refers to all of the following:

(a) hardware-only circuit implementations (such as implementations in only analog and/or digital circuitry), (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus to perform various functions, and (c) to circuits, such as a microprocessor(s) or a portion of a microprocessor(s), that require software or firmware for operation, even if the software or firmware is not physically present.

This definition of 'circuitry' applies to all uses of this term in this application, including in any claims. As a further example, as used in this application, the term "circuitry" would also cover an implementation of merely a processor (or multiple processors) or portion of a processor and its (or their) accompanying software and/or firmware.

Although embodiments of the present invention have been described in the preceding paragraphs with reference to various examples, it should be appreciated that modifications to the examples given can be made without departing from the scope of the invention as claimed. For example, in some embodiments of the invention, the applicator 57 does not rotate about the axis of rotation 70, and no third drive 53 is provided for causing the applicator 57 to rotate in this manner.

In some embodiments of the invention, a sensor may be provided to sense resistance to movement of the first guide 40 in the azimuthal dimension φ. The control circuitry 40 may be configured, in response to the sensor sensing resistance to movement of the first guide 40, to cause the first guide 40 to cease moving. This is a safety feature that prevents a person's limbs being trapped by the moving first guide 40.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

I claim:

1. A booth for applying product to the skin of a person, comprising:
   an entrance;
   an applicator configured to output the product;
   a guide configured to guide vertical movement of the applicator;
   a track;
   an arm, rotatably coupled to a roof of the booth, configured to move along the track;
   a first drive configured to drive the arm along the track, causing the arm to rotate the guide across the entrance of the booth into a plurality of different azimuthal positions;
   a second drive coupled to the applicator by a first link member and a second link member, the first link member extending along the arm and the second link member extending down the guide, wherein an aperture in the arm has a curved surface arranged to convert linear motion of the first link member into rotational motion of the second link member relative to the guide and rotational motion of the applicator relative to the guide; and
   control circuitry configured to
   control the first drive and the second drive.

2. The booth as claimed in claim 1, wherein the arm is configured to rotate about an axis of rotation aligned with a length of the guide.

3. The booth as claimed in claim 2, wherein the axis of rotation is separated from, and substantially parallel with, the length of the guide.

4. The booth as claimed in claim 2, wherein the applicator is configured to rotate about an axis that is perpendicular to the length of the guide, and the control circuitry is configured to control rotation of the applicator about the axis.

5. The booth as claimed in claim 2, wherein the second drive is configured to rotate the applicator, relative to the guide, about an axis that is substantially parallel to the axis of rotation of the arm.

6. The booth as claimed in claim 1, wherein the control circuitry is configured to control movement of the applicator in the guide and movement of the arm in accordance with a product application program.

7. The booth as claimed in claim 6, wherein the product application program used by the control circuitry depends on the weight of the person to whom the product is to be applied.

8. The booth as claimed in claim 6, wherein the product application program used by the control circuitry depends on the height of the person to whom the product is to be applied.

9. The booth as claimed in claim 1, further comprising: a sensor configured to sense the height of the person to whom the product is to be applied.

10. The booth as claimed in claim 1, further comprising:
a sensor configured to sense the weight of the person to whom the product is to be applied.

11. The booth as claimed in claim 1, further comprising:
a sensor configured to sense resistance to movement of the guide, wherein the control circuitry is configured, in response to the sensor sensing resistance to movement of the guide, to cause movement of the guide to cease.

12. The booth as claimed in claim 1, wherein the applicator is a spray gun configured to spray the product onto the skin of the person.

13. The booth as claimed in claim 1, wherein the control circuitry is configured, when the guide is in each of the azimuthal positions, to cause the applicator to move vertically in the guide and output the product.

14. The booth as claimed in claim 1, wherein the booth defines an inner volume and has the entrance that enables a person to enter the booth and position himself in the inner volume; and wherein the guide is positioned outside the entrance.

15. The booth as claimed in claim 1, wherein the control circuitry is configured to determine a height of a person, determine positions of various body parts of the person from at least the height of the person, and to control the applicator to move at different speeds in dependence upon the body part that the product is being applied to.

16. The booth as claimed in claim 1, wherein the control circuitry is configured to determine a body size of a person, the applicator is configured to rotate about an axis aligned with the guide, and the control circuitry is further configured to control rotation of the applicator about the axis in dependence upon on the determined body size of the person.

17. The booth as claimed in claim 1, wherein the control circuitry is configured to determine a body size of a person, and further configured to determine an angular range over which to rotate the arm in dependence upon the determined body size of the person.

18. The booth as claimed in claim 1, wherein the first drive is a stepper motor that is configured to drive the arm along the track in discrete steps, causing the arm to rotate the guide in discrete steps across the entrance of the booth.

19. A booth, for applying product to the skin of a person, comprising:
an entrance;
an applicator configured to output the product;
a guide configured to guide vertical movement of the applicator;
a track;
an arm, rotatably coupled to a roof of the booth, configured to move along the track;
a stepper motor configured to drive the arm along the track in discrete steps, causing the arm to rotate the guide across the entrance in discrete steps into a plurality of different azimuthal positions;
a drive coupled to the applicator by a first link member and a second link member, the first link member extending along the arm and the second link member extending down the guide, wherein an aperture in the arm has a curved surface arranged to convert linear motion of the first link member into rotational motion of the second link member relative to the guide and rotational motion of the applicator relative to the guide; and
control circuitry configured to control the stepper motor and the drive.

20. A booth, for applying product to the skin of a person, comprising:
an entrance;
an applicator configured to output the product;
a substantially vertical guide configured to guide vertical movement of the applicator;
a track comprising a rack;
an arm, rotatably coupled to a roof of the booth;
a stepper motor configured to drive the arm along the rack in discrete steps by rotating a pinion, causing the arm to rotate the guide in discrete steps about an axis of rotation across the entrance of the booth into a plurality of different azimuthal positions;
a linear drive, mounted on the arm and coupled to the applicator by a first link member and a second link member, the first link member extending along the arm and the second link member extending down the guide, wherein an aperture in the arm has a curved surface arranged to convert linear motion of the first link member into rotational motion of the second link member relative to the guide and rotational motion of the applicator relative to the guide, the rotational motion of the applicator being about a further axis of rotation that is spaced from and substantially parallel to the axis of rotation of the arm;
a further drive configured to drive vertical movement of the applicator along the guide; and
control circuitry configured to control the stepper motor, the linear drive and the further drive.

* * * * *